United States Patent [19]
Lewis et al.

[11] Patent Number: 5,420,112
[45] Date of Patent: May 30, 1995

[54] PREVENTION AND TREATMENT OF PERIPHERAL NEUROPATHY

[76] Inventors: Michael E. Lewis, 1007 Saber Rd., West Chester, Pa. 19382; Stuart C. Apfel, 218 Walker Pl., West Hempstead, N.Y. 11552; John A. Kessler, Wing Rd., New Canaan, Conn. 06840

[21] Appl. No.: 51,191

[22] Filed: Apr. 16, 1993

Related U.S. Application Data

[63] Continuation-in-part of Ser. No. 899,070, Jun. 12, 1992, abandoned.

[51] Int. Cl.$^6$ .................... A61K 38/00; A61K 38/04; A61K 38/08; A61K 38/22
[52] U.S. Cl. .......................... 514/12; 514/2; 514/21
[58] Field of Search ................ 514/2, 12, 21

[56] References Cited

U.S. PATENT DOCUMENTS

| | | | |
|---|---|---|---|
| 4,863,902 | 9/1989 | Amagase et al. | 514/12 |
| 5,068,224 | 11/1991 | Fryklund et al. | 514/21 |

FOREIGN PATENT DOCUMENTS

| | | |
|---|---|---|
| 0224885B1 | 5/1992 | European Pat. Off. . |
| WO89/05822 | 6/1989 | WIPO . |
| WO93/02695 | 2/1993 | WIPO . |

OTHER PUBLICATIONS

Guroff, G. Annals NY Academy of Sciences, 692 56–59 (1993) Exhibit 1.
Ekstrom et al. Ana NY Acad Sci 692: 291–93, (1993) Exhibit 2.
Apfel et al., "Nerve Growth Factor Prevents Toxic Neuropathy in Mice," Annals of Neurology 29:87–90, 1991.
Shiraishi et al., "The effect of Vincristine on Nerve Regeneration in the Rat: An Electrophysiological Study," Journal of the Neurological Sciences 71:9–17, 1985.
Bothwell, "Insulin and Somatemedin MSA Promote Nerve Growth Factor–Independent Neurite Formation by Cultured Chick . . . Neurons," Journal of Neuroscience Research 8:225–231, 1982.
Apfel et al. 1992, Ann. Neurol. 31:76–80.
Francis et al. 1992, Art to Science in Tissue Culture. Hyclone Laboratories Inc. 11:pp. 3, 5, 6, 7.
De Angelis et al. 1991, Cancer 67:2241–2246.
Olesen et al. 1991, Drug Safety 6:302–314.
Caroni et al. 1990, The Journal of Cell Biology 110:1307–1317.
Recio-Pinto et al. 1988, Neurochem. Int. 12:397;14 414.
Aizenman et al. 1987, Brain Research 406:32–42.
Ishii et al. 1987, In:Insulin, IGFs, and Their Receptors in the Central Nervous System (Raizada M. K. and Phillips M. A., eds), pp. 315–348. Plenum Press, New York.
Mengs et al. 1987, European Journal of Pharmacology 142:419–424.
Hansson et al. 1986, Acta. Physiol. Scand. 126:609–614.
Legha, Sewa S. 1986, Medical Toxicology 1:421–427.
Ross et al. 1981, The Journal of Neuroscience 1:1304—1311.

*Primary Examiner*—Howard E. Schain
*Assistant Examiner*—L. Touzeau

[57] ABSTRACT

The invention features a method of preventing or treating a peripheral neuropathy that results from a systemic disease (e.g., post-polio syndrome) or a toxic agent (e.g., a chemotherapeutic agent), and that is not caused by an abnormal insulin level in a mammal. The method involves administering a neuropathy-reducing amount of insulin-like growth factor-I (IGF-I) or insulin-like growth factor-III (IGF-III) to the mammal.

13 Claims, 5 Drawing Sheets

PREVENTION AND TREATMENT OF PERIPHERAL NEUROPATHY

This application is a Continuation-In-Part of U.S. Ser. No. 07/899,070 filed on Jun. 12, 1992, now abandoned.

BACKGROUND OF THE INVENTION

This invention relates to using an insulin-like growth factor-I to prevent or treat peripheral neuropathy.

Insulin like growth factor-I (IGF-I; somatomedin C) is a member of a family of structurally and functionally related polypeptides which also includes insulin, and insulin like growth factors II (IGF-II) and III (IGF-III). All of these protein factors may play a role in neuronal development and maintenance (Recio-Pinto, E., et al., 1988, Neurochem. Int. 12:397–414). In addition, there is evidence that the levels of IGF-I and IGF-II increase substantially during regeneration after sciatic nerve transection (Hansson, H. A., et al., 1986, Acta Physiol. Scand., 126:609–614). They have been shown to promote the survival of cultured sensory and sympathetic neurons (Ishii, D. N., et al., 1987, In: Insulin, IGFs and Their Receptors in the Central Nervous System, eds., Raizada, M. K., et al., Plenum Press, NY, pp. 315–348) and, in the case of IGF-I, to promote the survival of cortical neurons (Aizenman, Y., et al., 1987, Brain Res., 406:32–42). Finally, studies both in-vitro and in-vivo have demonstrated that IGF-I and IGF-II promote motor neuron survival and neurite outgrowth (Caroni, P., et al., 1990, J. Cell Biol., 110:1307–1317).

Peripheral neuropathy generally refers to a disorder that affects the peripheral nerves, most often manifested as one or a combination of motor, sensory, sensorimotor, or autonomic neural dysfunction. The wide variety of morphologies exhibited by peripheral neuropathies can each be uniquely attributed to an equally wide variety of causes. For instance, peripheral neuropathies can be genetically acquired, can result from a systemic disease, or can be induced by a toxic agent. Some toxic agents that cause neurotoxicities are therapeutic drugs, antineoplastic agents, contaminants in foods or medicinals, andenvironmental and industrial pollutants.

In particular, chemotherapeutic agents known to cause sensory and/or motor neuropathies include vincristine, an antineoplastic drug used to treat haematological malignancies and sarcomas. The neurotoxicity is dose-related, and exhibits as reduced intestinal motility and peripheral neuropathy, especially in the distal muscles of the hands and feet, postural hypotension, and atony of the urinary bladder. Similar problems have been documented with taxol and cisplatin (Mollman, J. E., 1990, New Eng Jour Med. 322:126–127), although cisplatin-related neurotoxicity can be alleviated with nerve growth factor (NGF) (Apfel, S. C. et al., 1992, Annals of Neurology 31:76–80). Although the neurotoxicity is sometimes reversible after removal of the neurotoxic agent, recovery can be a very slow process (Legha, S., 1986, Medical Toxicology 1:421–427; Olesen, et al., 1991, Drug Safety 6:302–314).

There are a number of inherited peripheral neuropathies, including: Refsum's disease, Abetalipoproteinemia, Tangier disease, Krabbe's disease, Metachromatic leukodystrophy, Fabry's disease, Dejerine-Sottas syndrome, and others. Of all the inherited neuropathies, the most common by far is Charcot-Marie-Tooth Disease.

Charcot-Marie-Tooth (CMT) Disease (also known as Peroneal Muscular Atrophy, or Hereditary Motor Sensory Neuropathy (HMSN)) is the most common hereditary neurological disorder. It is characterized by weakness and atrophy, primarily of the peroneal muscles, due to segmental demyelination of peripheral nerves and associated degeneration of axons and anterior horn cells. Autosomal dominant inheritance is usual, and associated degenerative CNS disorders, such as Friedreich's ataxia, are common.

There are two primary forms of CMT Disease. Type I (70% of cases) was believed to have demyelination as its initial pathophysiology, but distal clinical involvement suggests a primary axonal degeneration, as in Type II. Type II (30% of cases) is primarily an axonal degeneration without demyelination, and may not be as severe as Type I. Nerve conduction impairment is often present at birth, though this is not a predictor of the possible age of onset or severity of progression. There are also very rare, Type III and Type IV forms, which are recessively-linked.

SUMMARY OF THE INVENTION

The invention features a method of reducing a peripheral neuropathy that is not caused by an abnormal insulin level in a mammal. The method involves administering a neuropathy-reducing amount of insulin-like growth factor-I (IGF-I) or insulin-like growth factor-III (IGF-III) to the mammal.

In various preferred embodiments, the mammal is a human, or an agricultural or domestic mammal that develops a neuropathy, e.g., as a result of treatment of a neoplasm with a chemotherapeutic agent. IGF-I or IGF-III can be administered in a manner deemed effective by one skilled in the art; preferred modes of administration are intravenous administration and subcutaneous injection.

As used herein, "peripheral neuropathy" refers to a disorder affecting a segment of the peripheral nervous system. The invention involves using IGF-I or IGF-III, members of the insulin family of growth factors, to reduce a neurotoxicity that is not obviously or directly caused by an abnormal level of insulin, including, but not limited to, distal sensorimotor neuropathy, or autonomic neuropathies such as reduced motility of the gastrointestinal tract or atony of the urinary bladder. Preferred neuropathies that can be effectively treated with IGF-I or IGF-III include neuropathies associated with systemic disease, e.g., post-polio syndrome; genetically acquired neuropathies, e.g., Charcot-Marie-Tooth disease; and neuropathies caused by a toxic agent, e.g., a chemotherapeutic agent, preferably vincristine.

Where IGF-I or IGF-III is used to treat a neuropathy induced by a toxic agent, it can be administered before, simultaneously with, or after exposure to the toxic agent, or before, during or after administration of a chemotherapeutic. Preferably, the IGF-I and the chemotherapeutic agent are each administered at effective time intervals, during an overlapping period of treatment. The IGF-I or IGF-III can be administered to the mammal following exposure to the neurotoxic agent, or following chemotherapy, to restore at least a portion of the neurofunction destroyed by the neurotoxic agent or chemotherapeutic. The chemotherapeutic can be any chemotherapeutic agent that causes neurotoxicity, preferably vincristine, taxol, dideoxyinosine, or cisplatin. In a preferred example, the weight to weight ratio of IGF-I or IGF-III (des-(1-3)IGF-I), to vincristine is between 1:400 and 75:1, preferably between 1:40 and 8:1.

Where IGF-I and a chemotherapeutic agent are administered simultaneously, the invention features a composition that includes a substantially pure IGF-I and a chemotherapeutic agent, in a weight to weight ratio of between 1:400 and 75:1. The chemotherapeutic agent is preferably vincristine, cisplatin, dideoxyinosine, or taxol. The term "substantially pure" as used herein, refers to IGF-I or IGF-III which, prior to mixing with another component of the composition, is at least 50% (by weight) of the protein present in the preparation. In preferred embodiments, at least 75%, more preferably at least 90%, and most preferably at least 99% (by weight) of the protein present in the preparation is IGF-I or IGF-III. Most preferably, the IGF-I or IGF-III used in the composition of the invention is pure as judged by amino-terminal amino acid sequence analysis.

By "toxic agent" or neurotoxic agent, is meant a substance that through its chemical action injures, impairs, or inhibits the activity of a component of the nervous system. The list of neurotoxic agents that cause neuropathies is lengthy, and includes, but is not limited to, neoplastic agents such as vincristine, vinblastine, cisplatin, taxol, or dideoxy- compounds, e.g., dideoxyinosine; alcohol; metals; industrial toxins involved in occupational or environmental exposure; contaminants of food or medicinals; or over-doses of vitamins or therapeutic drugs, e.g., antibiotics such as penicillan or chloramphenicol, or megadoses of vitamins A, D, or B6. An extensive, although not complete, list of chemical compounds with neurotoxic side-effects is found in Table 5. Although this list provides examples of neurotoxic compounds, it is intended to exemplify, not limit, the scope of the invention. Other toxic agents can cause neuropathies, and can be characterized by methods known to one skilled in the art. By "exposure to a toxic agent" is meant that the toxic agent is made available to, or comes into contact with, a mammal of the invention. Exposure to a toxic agent can occur by direct administration, e.g., by ingestion or administration of a food, medicinal, or therapeutic agent, e.g., a chemotherapeutic agent, by accidental contamination, or by environmental exposure, e.g., aerial or aqueous exposure.

The terms IGF-I and IGF-III include fragments or analogs thereof that exhibit the biological activity of the invention, i.e., the ability to reduce a neuropathy induced by a toxic agent. Methods of determining whether an IGF-I or IGF-III fragment or analog possesses the biological activity of the invention are described below. Generally, suitable analogs and fragments will share at least 65% homology with naturally occurring IGF-I or IGF-III. The fragment polypeptides of IGF-I or IGF-III are subsets of the IGF-I, or IGF-III molecules (respectively), containing fewer amino acid residues than the native molecules. As used herein, a fragment of IGF-I or IGF-III can ordinarily be at least about 5 contiguous amino acids, and can be at least about 30–40 amino acids in length, and preferably about 50–65 amino acids in length. Preferred sequences are of 6–25 residues. A portion of the amino acids of the fragment may be substituted with conservative replacements or deletions which improve the chemical or biological stability of the product peptides. Preferably, no more than 35%, and more preferably no more than 20%, of the amino acid residues are replaced or deleted. The following examples of preferred IGF-I sequences fall within the scope of the invention: 1) IGF-I (55–70)- (SEQ ID NO:1), described in a co-assigned patent application by Lewis et al. U.S. Ser. No. 07/869,913); and 2) Long $R^3$ IGF-I, which is a fusion protein that consists of human IGF-I with a 13 amino acid extension peptide at the N-terminus and the substitution of Arg for Glu at position 3 (Francis, G. L, et al. 1992. Art to Sci. in Tissue Culture. HyClone Laboratories, Inc. 11:3–7; GROPEP PTY.LTD. PCT Appl. WO89/05822; U.S. Pat. No. 5,164,370; PCT/AU90/00210). The peptide fragments listed herein are examples only, and do not limit the scope of IGF-I peptide fragments useful in the invention.

"Homology", as used herein, refers to the sequence similarity between two polypeptide molecules. When a position in both of the two compared sequences is occupied by the same amino acid monomeric subunit, e.g., if a position in each of two polypeptide molecules is occupied by lysine, then the molecules are homologous at that position. The homology between two sequences is a function of the number of matching or homologous positions shared by the two sequences. For example, if 6 of 10 of the positions in two sequences are matched or homologous, then the two sequences are 60% homologous. By way of example, the amino acid sequences LTVSFR and LPVSAT share 50% homology.

An analog of IGF-I or IGF-III can differ from a naturally occurring IGF-I or IGF-III by conservative amino acid sequence differences or by modifications that do not affect sequence, or by both. Modifications include chemical derivatization of polypeptides, e.g., acetylation, carboxylation, glycosylation, or phosphorylation; substitution or deletion of amino acid residues that alter the binding protein affinity but do not substantially alter the receptor affinity and/or alter the biological activity of the polypeptide; or chemical alterations to the polypeptide that increase polypeptide stability.

Despite the widely disparate morphologies and causes attributed to peripheral neuropathies in vivo, applicants have hypothesized that IGF-I can be an effective means of preventing or treating such neuropathies in a mammal, despite the fact that these neuropathies can not be directly or obviously linked to a deficiency in, or otherwise abnormal level of, insulin. To illustrate this, applicants have shown that administering IGF-I to animals given a drug with neurotoxic side effects, i.e., the anti-tumor drug vincristine, reduces the associated neurotoxicity. This finding not only alleviates the neurotoxic side-effect, but could also substantially increase the use of vincristine as an anti-tumor agent. The use of vincristine, an otherwise effective chemotherapeutic, has heretofore been limited by accompanying neurotoxicity. This finding could also similarly increase the use of other compounds limited by neurotoxicity problems. Co-administration of IGF-I or IGF-III can decrease the occurrence of these accompanying peripheral neuropathies.

Other features and advantages of the invention will be apparent from the following description of the preferred embodiments and from the claims.

DETAILED DESCRIPTIONS

The drawings will first be described.

Drawings

DESCRIPTION OF THE INVENTION

Figure 1:
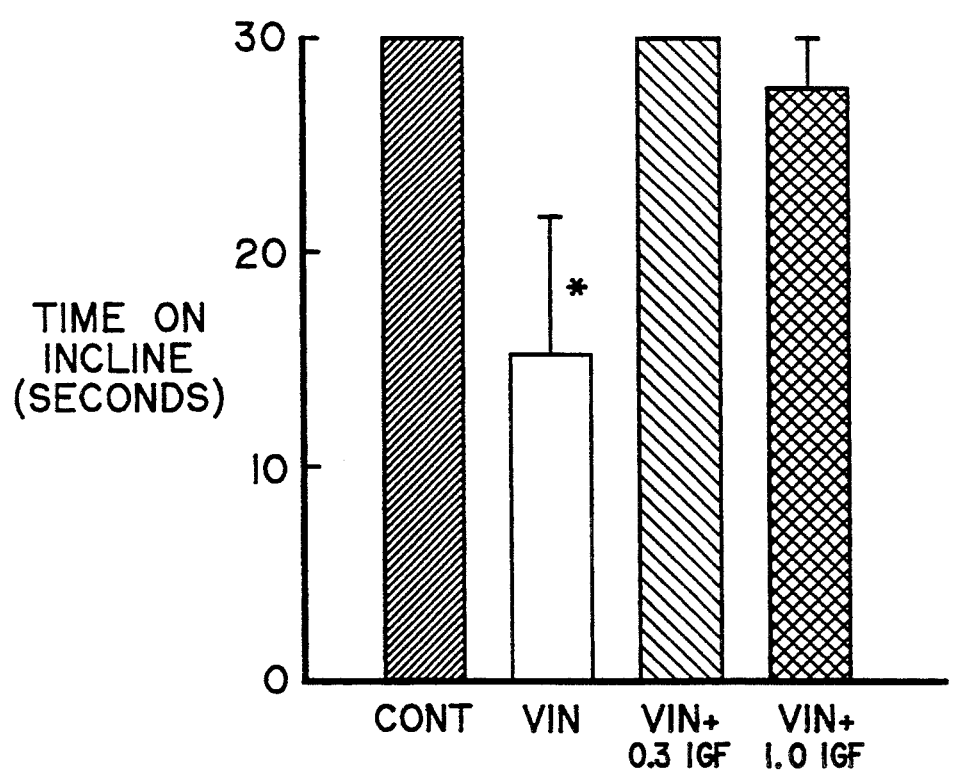
FIG. 1 is a bar graph showing the effect of rhIGF-I on motor function after vincristine treatment in mice.

It occurred to applicants that IGF-I, as well as IGF-I related proteins and peptides, might promote the functioning and/or survival of neurons otherwise at risk of losing function and/or dying due to exposure to toxic agents. To specifically test this idea, applicants have investigated whether IGF-I administration is capable of preventing the neurotoxicity resulting from administration of the anti-tumor agent vincristine in an animal model. Clinically, the usefulness of vincristine is limited by the occurrence of polyneuropathy with prominent motor dysfuntion, as well as sensory and autonomic abnormalities (Legha, S. S., supra). To date, there is no effective means of preventing this neuropathy short of limiting the dose of vincristine. Applicants have demonstrated that IGF-I administration is capable of preventing this debilitating and dose-limiting side effect of vincristine.

In a second test of this idea, applicants have investigated whether IGF-I administration is capable of preventing the neurotoxicity resulting from administration of the antitumor agent taxol in an animal model.

EXPERIMENTAL EXAMPLE: VINCRISTINE

Methods

Drug Administrations

Vincristine sulfate (Sigma Chemical, St. Louis, Mo.) was administered at a dose of 2 mg/kg intraperitoneally twice a week for six consecutive weeks. It was formulated at a concentration of 0.16 mg/ml normal saline.

Recombinant IGF-I (rhIGF-I) for experimental use was provided by Cephalon Inc. (West Chester, Pa.), and it is also commercially available from RD Systems, Inc. (Minneapolis, Minn.), U. B. I. (Lake Placid, N.Y.), and Kabi Pharmacia AS (Stockholm, Sweden). The rhIGF-I was formulated for the high dose group at a concentration of 1 mg/ml, and for the low dose group at a concentration of 0.3 mg/ml, in an acetic acid buffer solution with a pH of 6.0. The high dose groups (Groups 4 and 6) received 1.0 mg/kg IGF-I three times a week subcutaneously for six consecutive weeks. The low dose treated groups (Groups 3 and 5) received 0.3 mg/kg IGF-I three times a week subcutaneously for the same period of time. Groups not receiving IGF-I received subcutaneous injections of the acetic acid buffer vehicle in the same volume per weight, and according to the same schedule, as the animals receiving IGF-I.

Animals

CD1 male mice weighing between 15–20 gms at the outset were selected for this study. They were randomly distributed, 12 animals to each of the following treatment groups:

Group #1: Control, vehicle injections only.
Group #2: Vincristine plus IGF-I vehicle.
Group #3: Vincristine plus low dose IGF-I.
Group #4: Vincristine plus high dose IGF-I.
Group #5: Low dose IGF-I alone.
Group #6: High dose IGF-I alone.

Behavioral Testing

Incline test: After 6 weeks of treatment, the mice were tested in a blinded fashion. For this test each mouse was placed individually on a styrofoam board, which was then raised to a vertical position. The animals were timed for how long they could maintain their grip on the board without falling. The test was arbitrarily stopped after 30 seconds. The best time out of three trials was recorded.

Electrophysiological Testing

After behavioral testing, the mice underwent electrophysiological testing. Each mouse was anesthetized with halothane before recording. Compound amplitudes and distal latencies were measured in the caudal nerve of the tail. The tails were restrained and platinum-iridium needle surface electrodes were placed along the distal section of the caudal nerve. The active recording electrode was positioned at a fixed distance of 40 mm distal to the stimulating cathode. Brief pulses of constant voltage stimulation were delivered through an anode-cathode pair positioned overlying a proximal section of the caudal nerve. Motor recordings were conducted orthodromically from the tibial nerve with electrode placement over the distal insertion of the gastrocnemius muscle. Sensory recordings were conducted orthodromically from the sural nerve with a distance of 10 mm between electrodes. For each recording five to ten stimuli were averaged, and the procedure was repeated. Latency was determined from the onset of the initial depolarization and was measured to the nearest 0.1 msec. Amplitude was measured from the baseline to peak and was measured to the nearest 0.1 $\mu$V. Rectal temperature of each mouse was monitored and maintained within 0.5° C.

Statistics

Data were analyzed using an analysis of variance (ANOVA) in all cases.

Results

Behavioral Testing

Clinically, vincristine causes a mixed sensory-motor neuropathy, with distal motor weakness as the most prominent early sign. We therefore made use of a simple behavioral test to ascertain the motor strength of the animals in each group. The data from the incline test are summarized in Table 1 and FIG. 1. The animals treated with vincristine alone were able to maintain their grip for only about half the maximal time. The other groups tested were all able to maintain their grips for approximately the full 30 seconds allowed. The vincristine alone treated group differed from the other groups with a $p < 0.0001$ by ANOVA.

Electrophysiological Results

Figure 2:
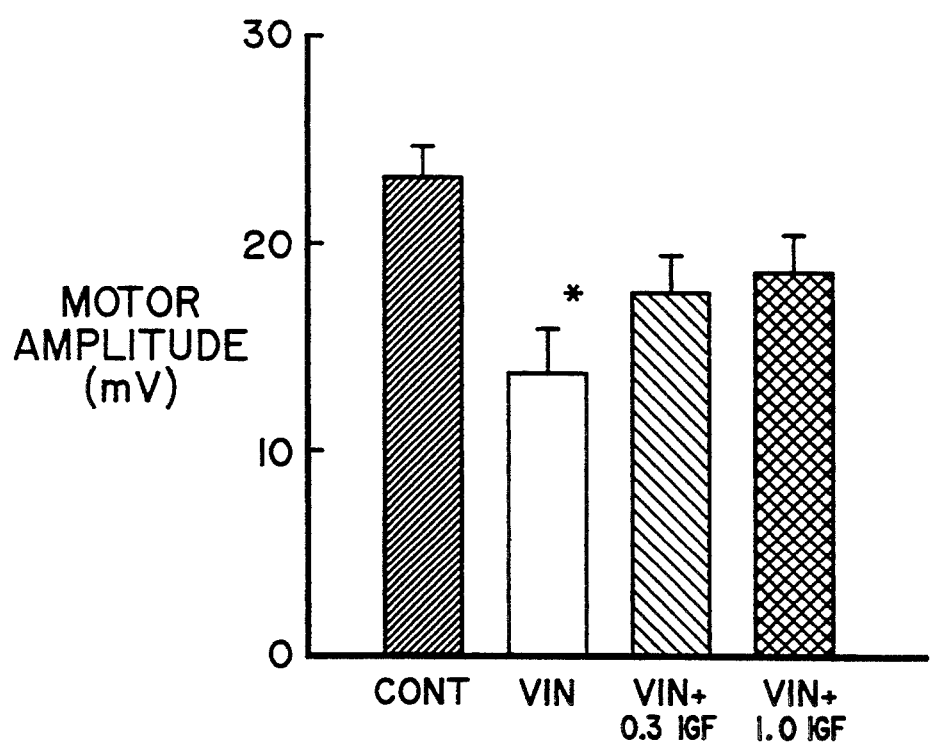
FIG. 2 is a bar graph showing the effect of rhIGF-I on tibial nerve function after vincristine treatment in mice.

Motor conduction was measured from the tibial nerve, and the results are summarized in Table 2 and FIG. 2. The group treated with vincristine alone had a prolonged latency and a significantly reduced action potential amplitude as compared to the control group ($p < 0.02$ by ANOVA). The groups co-treated with IGF-I did not differ significantly from the control group.

Figure 3:
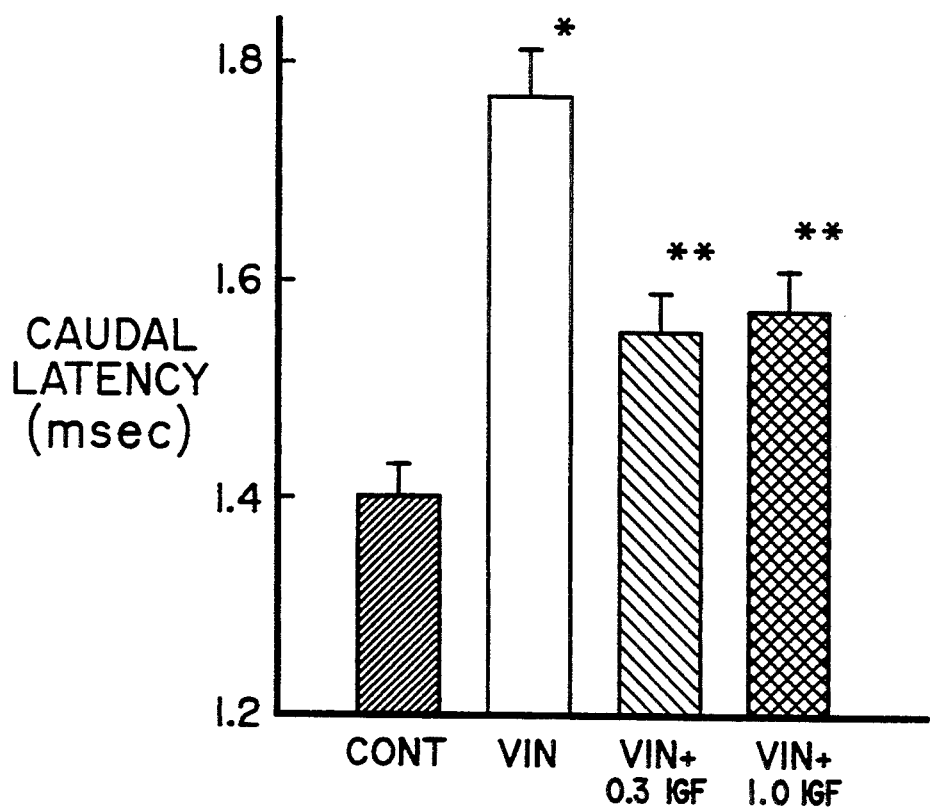
FIG. 3 is a bar graph showing the effect of rhIGF-I on caudal nerve function after vincristine treatment in mice.

Compound recordings were conducted from the caudal nerve in the tail and the results are summarized in Table 3 and FIG. 3. Here too, the vincristine alone treated group had significantly prolonged latencies and reduced amplitudes ($p<0.001$ and $p<0.05$ respectively). In each case IGF-I administration partially though not completely improved upon these values.

Sensory recordings were conducted from the sural nerve and the values summarized in Table 4. There were no statistically significant differences between any of the groups as determined by this measurement of purely sensory function.

The data presented indicate that co-administration of IGF-I with vincristine can prevent the manifestations of vincristine neuropathy seen in this animal model. Applicants have demonstrated the presence of neuropathy using both behavioral and electrophysiological measurements. This animal model of vincristine neuropathy appears to correlate well with the human clinical condition in that motor dysfunction is the most prominent manifestation. Wherever vincristine administration impaired the function of the peripheral nerve, IGF-I administration resulted in a significant improvement.

EXPERIMENTAL EXAMPLE: TAXOL

To assess whether rhIGF-I could prevent development of a sensory neuropathy caused by taxol administration, male CD-1 mice were dosed daily with taxol (21.6 mg/kg) administered intraperitoneally for 6 days in taxol-vehicle (12% chromophore EL (Sigma, St. Louis Mo.), 76% phosphate-buffered saline, 12% ethanol). rhIGF-I vehicle (100 mM acetic acid, 50 mM NaCl, 1% human serum albumin) or rhIGF-I (1 mg/kg) was administered subcutaneously for 10 days beginning one day prior to the start of the taxol injections. On the last day of rhIGF-I vehicle or rhIGF-I administration, the ability of mice to sense and respond to a noxious stimulus was assessed by determining hot-plate (55° C.) and tail-flick latencies (D'Amour et al. J. Pharmacol. Exp. Ther. 72:74–79, 1941; Eddy et al. J. Pharmacol. Exp. Ther. 107:385–393, 1953; Vaught et al. Life Sci. 48:2233–2241, 1991). Hot-plate and tail-flick latencies were determined twice for each mouse. The cutoff time to lick one hindpaw or shake a hindpaw three times in the hot-plate assay was 20 sec and to move its tail from a heated coil in the tail-flick assay was 10 sec. Significant differences between vehicle and taxol-treatment groups were determined by Dunnett's t-test (Tallarida et al. *Manual of Pharmacologic Calculation with Computer Programs*, 2nd ed. Springer-Verlag, NY, pp. 145–148, 1987) and differences between all groups by a Newman-Keul's test (Tallarida et al. supra, pp. 121–125).

Only the mice treated with taxol/rhIGF-I vehicle had tail-flick and hot plate latencies that were significantly greater than that of vehicle-treated mice. Taxol significantly increased tail-flick and hot-plate latencies 43% and 37%, respectively. In addition, the tail-flick and hot-plate latencies for the taxol-treated mice were also significantly greater than that of mice treated with rhIGF-I or taxol/rhIGF-I. Thus, rhIGF-I prevented the development of a sensory neuropathy as measured by changes in tail-flick and hot-plate latencies.

Figure 4:
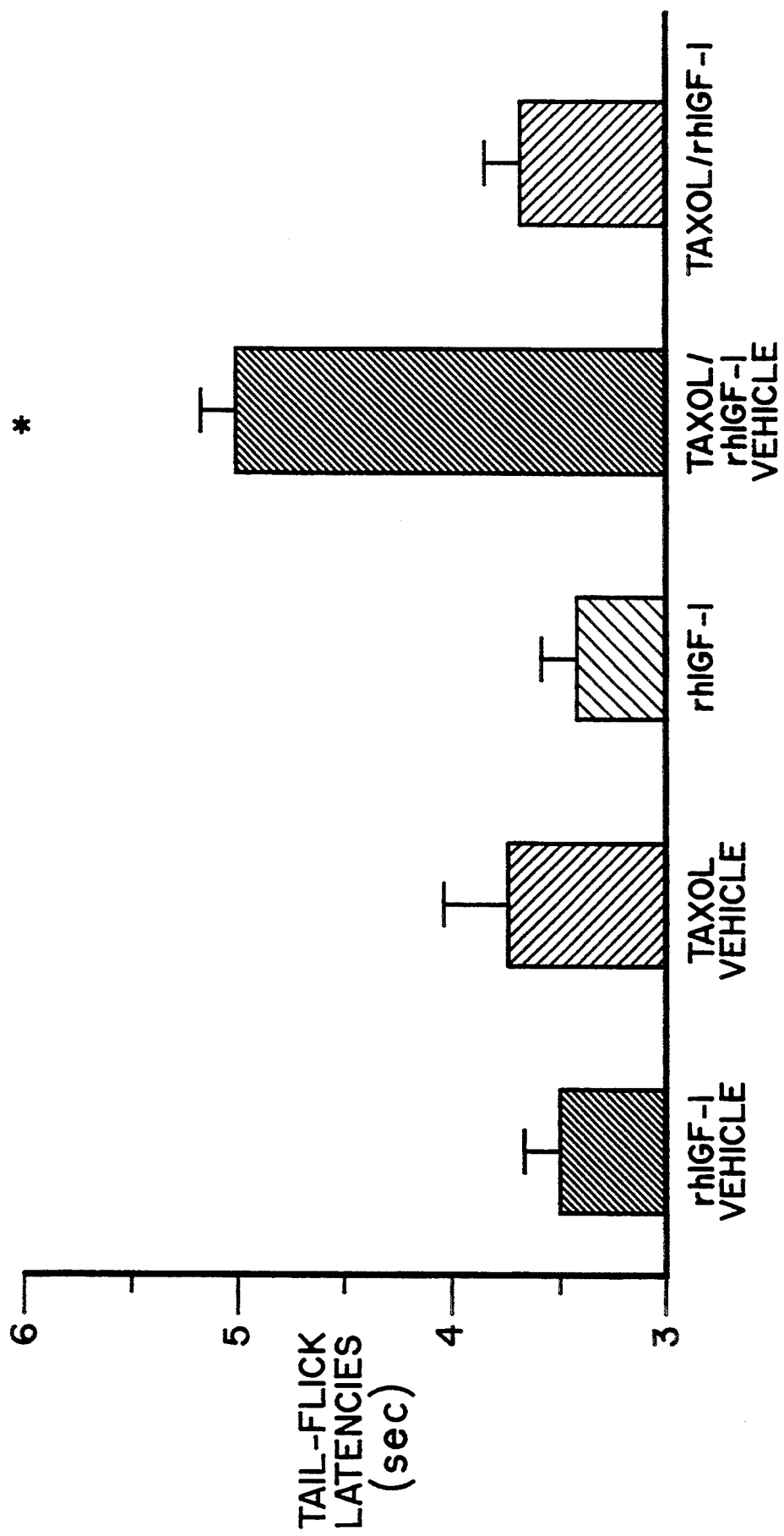
FIG. 4 is a bar graph showing the effect of taxol and rhIGF-I on tail-flick latencies in mice.
Figure 5:
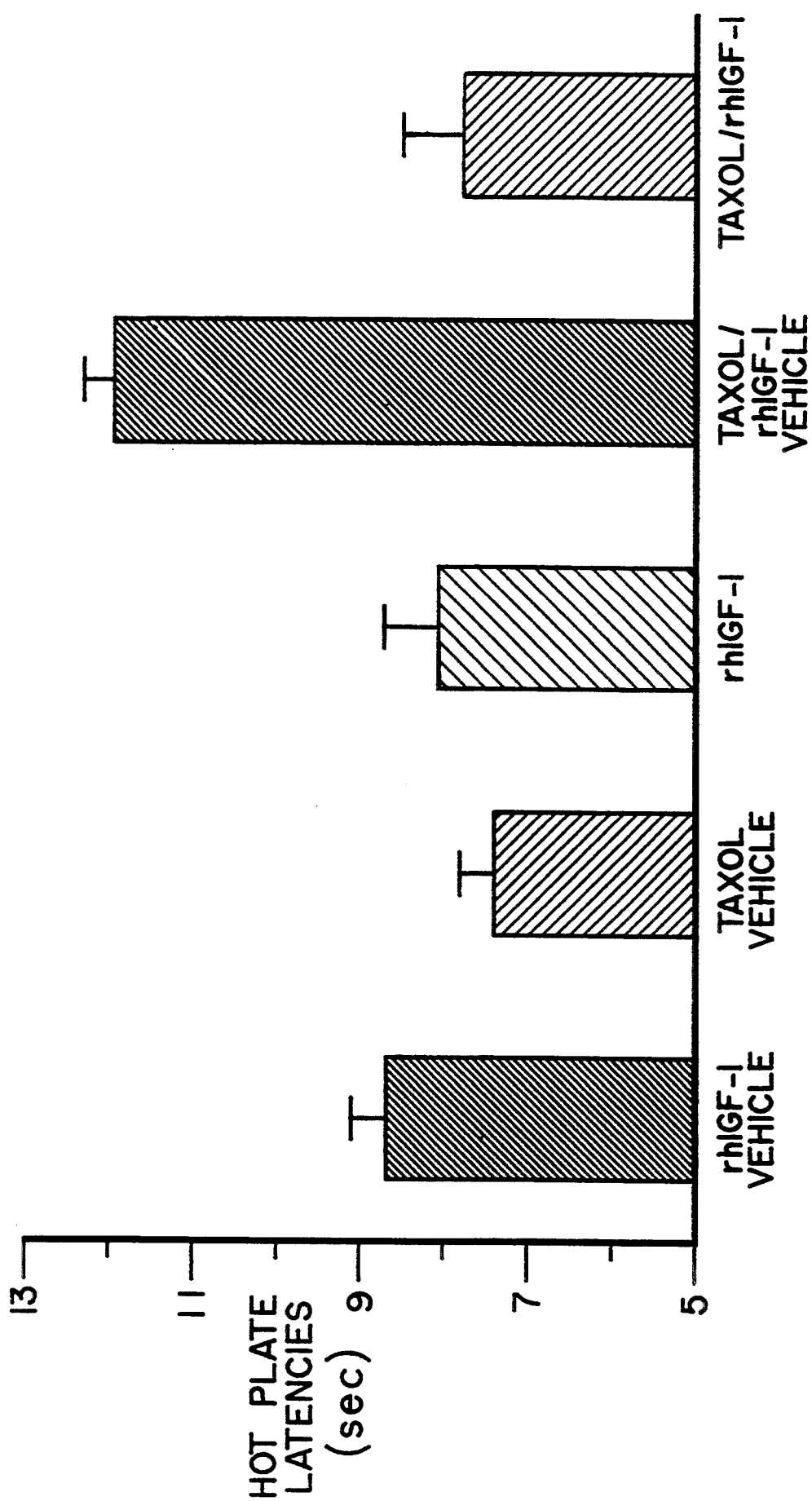
FIG. 5 is a bar graph showing the effect of taxol and rhIGF-I on hot plate latencies in mice.

The effect of rhIGF-I administration on preventing taxol-induced neuropathy is shown in Table 6, in FIG. 4 (tail-flick latencies) and in FIG. 5 (hot plate latencies). Results are presented as mean+Standard Error of the Mean (S.E.M.). The symbol * denotes rhIGF-I alone, and taxol/rhIGF-I-treated groups $p<0.05$.

Therapy

Any of the IGF-I neuropathy-reducing agents described herein can be administered to a patient in a pharmaceutically-acceptable buffer (e.g., physiological saline or acetic acid buffer). Although it may be convenient to administer IGF-I or IGF-III subcutaneously, orally, nasally, or topically, e.g., as a liquid or spray, the therapeutic preparation is administered in accordance with the condition to be treated. For example, it may be necessary to administer IGF-I intravenously, or surgically to the appropriate tissue, or via a catheter.

An appropriate dosage is an amount of an insulin-like growth factor-I, fragment or analog which effects a reduction in the extent of neuropathy. IGF-I, for example, can be administered at dosages of 0.03–10 mg/kg/unit dose, as a bolus or by infusion, administered either daily, intermittently, or according to need. This dosage corresponds approximately to the weight to weight ratio of IGF-I to vincristine of between 1:400 and 75:1, preferably 1:40 to 8:1. Dosages of other insulin-like growth factor-I's, fragments or analogs, or their weight to weight ratios relative to the toxic agent of instance, can be determined by one skilled in the art, according to the methods described herein.

The effectiveness of treating neuropathies with IGF-I can be evaluated by the following signs of recovery: 1) Recovery of normal sensory function, which can be assessed by thermal sensitivity of the extremities; 2) Recovery of normal motor function, which can be assessed by measures of muscle weakness, fine motor control, and deep tendon reflexes; and 3) Normalization of nerve conduction velocity, which is assessed electrophysiologically. Methods for assessing peripheral neuropathy are described by Asbury et al. (Asbury et al., 1992, in *Diseases of the Nervous System, Clinical Neurobiology*, eds. Asbury et al. W. B. Saunders Inc. Philadelphia, Pa. 1:252–269) and can be employed by those skilled in the art to determine the effectiveness of an insulin-like growth factor-I in alleviating neuropathy.

Other Embodiments

Other embodiments are within the following claims. For example, agents useful in reducing toxic neuropathy can include any of the family of insulin-like growth factor-I's and related neurotrophins, nerve growth factor-enhancing molecules, ciliary neurotrophic factor, IGF-I derived peptide fragments, analogs of an insulin-like growth factor-I, or combinations of these agents.

While vincristine neurotoxicity most typically is manifested as a peripheral neuropathy, the method of the invention can also be used to reduce other toxic neuropathies, e.g., neuropathies of the autonomic or cranial nervous systems, and can be used to mitigate the effects of other toxic agents.

The invention further includes neuropathies associated with systemic diseases: uremia, childhood cholestatic liver disease, chronic respiratory insufficiency, alcoholic polyneuropathy, multiple organ failure, sepsis, hypoalbuminemia, eosinophilia-myalgia syndrome, hepatitis, porphyria, hypoglycemia, vitamin deficiency, chronic liver disease, primary biliary cirrhosis, hyperlipidemia, leprosy, Lyme disease, herpes zoster, Guillain-Barre syndrome, chronic inflammatory demyelinating polyradiculoneuropathy, sensory perineuritis, acquired immunodeficiency syndrome (AIDS)-associated neuropathy, Sjogren's syndrome, primary vasculitis (such as polyarteritis nodosa), allergic granulomatous angiitis (Churg-Strauss), hypersensitivity angiitis, Wegener's granulomatosis, rheumatoid arthritis, systemic lupus erythematosis, mixed connective tissue disease, scleroderma, sarcoidosis, vasculitis, systemic vasculitides, acute inflammatory demyelinating polyneuropathy, post-polio syndrome, carpal tunnel syndrome, pandysautonomia, primary systemic amyloidosis, hypothyroidism, chronic obstructive pulmonary disease, acromegaly, malabsorption (sprue, celiac disease), carcinomas (sensory, sensorimotor, late and demyelinating), lymphoma (including Hodgkin's), polycythemia vera, multiple myeloma (lytic type, osteosclerotic, or solitary plasmacytoma), benign monoclonal gammopathy, macroglobulinemia, and cryoglobulinemia, as described by Asbury et al. supra, herein incorporated by reference.

The invention also includes genetically acquired neuropathies: peroneal muscular atrophy (Charcot-Marie-Tooth Disease, types I, II, and X),hereditary amyloid neuropathies, hereditary sensory neuropathy (type I and type II), porphyric neuropathy, hereditary liability to pressure palsy, Fabry's disease, adrenomyeloneuropathy, Riley-Day syndrome, Dejerine-Sottas neuropathy (hereditary motor-sensory neuropathy-III), Refsum's disease, ataxia-telangiectasia, hereditary tyrosinemia, anaphalipoproteinemia, abetalipoproteinemia, giant axonal neuropathy, metachromatic leukodystrophy, globoid cell leukodystrophy, and Friedrich's ataxia (Asbury et al. supra). Also included in the invention are mononeuropathy multiplex, plexopathy, and pure motor neuropathy, as described by Asbury et al. supra.

TABLE I

| GROUP | INCLINE TEST (sec) MEANS | S.E.M. |
|---|---|---|
| CONTROL | 27.6 | 2.4 |
| VIN ALONE | 15.4* | 6.5 |
| VIN + IGF LOW | 30 | 0 |
| VIN + IGF HIGH | 27.7 | 2.3 |
| IGF LOW | 30 | 0 |
| IGF HIGH | 27 | 3 |

Data from the incline test. Values represent the time the animals could remain suspended from a verticle incline, with a maximum set at 30 seconds.
*Means this value differed from the other groups with a $p < 0.0001$

TABLE 2

| | TIBIAL - MOTOR NERVE | | | |
|---|---|---|---|---|
| | LATENCY (msec) | | AMPLITUDE (mV) | |
| GROUP | MEAN | S.E.M. | MEAN | S.E.M. |
| CONTROL | 1.21 | 0.03 | 22.98 | 1.06 |
| VIN ALONE | 1.35 | 0.05 | 13.94* | 2.11 |
| VIN + IGF LOW | 1.38 | 0.05 | 17.12 | 1.53 |
| VIN + IGF HIGH | 1.43 | 0.08 | 18.48 | 1.89 |
| IGF LOW | 1.21 | 0.02 | 19.8 | 1.81 |
| IGF HIGH | 1.23 | 0.03 | 20.76 | 1.47 |

Electrophysiological measurements from the tibial nerve.
*Signifies that this group differed from the control with a $p < 0.02$.

TABLE 3

| | CAUDAL - COMPOUND NERVE | | | |
|---|---|---|---|---|
| | LATENCY (msec) | | AMPLITUDE (mV) | |
| GROUP | MEAN | S.E.M. | MEAN | S.E.M. |
| CONTROL | 1.39 | 0.03 | 57.32 | 3.47 |
| VIN ALONE | 1.74** | 0.09 | 30.66* | 8.56 |
| VIN + IGF LOW | 1.55* | 0.03 | 37.01* | 2.59 |
| VIN + IGF HIGH | 1.58* | 0.03 | 36.05* | 1.65 |
| IGF LOW | 1.46 | 0.03 | 55.93 | 5.68 |
| IGF HIGH | 1.45 | 0.03 | 51.96 | 4.25 |

Electrophysiological measurements from the caudal nerve.
*Signifies that these values differed from the control with a $p < 0.05$.
**Signifies that this value differed from the control with a $p < 0.001$.

TABLE 4

| | SURAL - SENSORY NERVE | | | |
|---|---|---|---|---|
| | LATENCY (msec) | | AMPLITUDE (mV) | |
| GROUP | MEAN | S.E.M. | MEAN | S.E.M. |
| CONTROL | 0.54 | 0.01 | 35.29 | 3.55 |
| VIN ALONE | 0.62 | 0.04 | 55.66 | 7.46 |
| VIN + IGF LOW | 0.61 | 0.02 | 44.49 | 7.09 |
| VIN + IGF HIGH | 0.57 | 0.03 | 37.27 | 5.4 |
| IGF LOW | 0.55 | 0.02 | 30.52 | 3.34 |
| IGF HIGH | 0.5 | 0.02 | 43.06 | 7.73 |

Electrophysiological measurements from the sural nerve. There were no statistically significant differences among groups.

TABLE 5

| AGENTS THAT CAUSE PERIPHERAL NEUROPATHY | |
|---|---|
| AGENT | ACTIVITY |
| acetazolamide | diuretic |
| acrylamide | flocculent, grouting agent |
| adriamycin | antineoplastic |
| alcohol (ethanol) | solvent, recreational drug |
| almitrine | respiratory stimulant |
| amiodarone | antiarrhythmic |
| amphotericin | antimicrobial |
| arsenic | herbicide, insecticide |
| aurothioglucose | antirheumatic |
| barbiturates | anticonvulsant, sedative |
| buckthorn | toxic berry |
| carbamates | insecticide |
| carbon disulfide ($CS_2$) | industrial |
| chloramphenicol | antibacterial |
| chloroquine | antimalarial |
| cholestyramine | antihyperlipoproteinemic |
| cisplatin | antineoplastic |
| clioquinol | amebicide, antibacterial |
| colestipol | antihyperlipoproteinemic |
| colchicine | gout suppressant |
| colistin | antimicrobial |
| cycloserine | antibacterial |
| cytarabine | antineoplastic |
| dapsone | dermatologic including leprosy |
| dideoxycytidine | antineoplastic |
| dideoxyinosine | antineoplastic |
| dideoxythymidine | antiviral |
| disulfiram | antialcohol |
| doxorubicin | antineoplastic |
| ethambutol | antibacterial |
| ethionamide | antibacterial |
| glutethimide | sedative, hypnotic |
| gold | antirheumatic |
| hexacarbons | solvents |
| hormonal contraceptives | |
| hexamethylolmelamine | fireproofing, creaseproofing |
| hydralazine | antihypertensive |
| hydroxychloroquine | antirheumatic |
| imipramine | antidepressant |
| indomethacin | anti-inflammatory |
| inorganic lead | toxic metal in paint, etc. |
| isoniazid | antituberculous |
| lithium | antidepressant |
| methylmercury | industrial waste |
| metformin | antidiabetic |
| methylhydrazine | synthetic intermediate |
| metronidazole | antiprotozoal |
| misonidazole | radiosensitizer |
| nitrofurantoin | urinary antiseptic |
| nitrogen mustard | antineoplastic, nerve gas |

TABLE 5-continued

AGENTS THAT CAUSE PERIPHERAL NEUROPATHY

| AGENT | ACTIVITY |
|---|---|
| nitrous oxide | anesthetic |
| organophosphates | insecticides |
| ospolot | anticonvulsant |
| penicillin | antibacterial |
| perhexiline | antiarrhythmic |
| perhexiline maleate | antiarrhythmic |
| phenytoin | anticonvulsant |
| platinum | drug component |
| primidone | anticonvulsant |
| procarbazine | antineoplastic |
| pyridoxine | vitamin B6 |
| sodium cyanate | anti-sickling |
| streptomycin | antimicrobial |
| sulphonamides | antimicrobial |
| suramin | antineoplastic |
| tamoxifen | antineoplastic |
| taxol | antineoplastic |
| thalidomide | antileprous |
| thallium | rat poison |
| triamterene | diuretic |
| trimethyltin | toxic metal |
| L-tryptophan | health food additive |
| vincristine | antineoplastic |
| vinblastine | antineoplastic |
| vindesine | antineoplastic |
| vitamin A | mega doses |
| vitamin D | mega doses |

TABLE 6

EFFECT OF TAXOL AND rhIGF-I ON TAIL-FLICK AND HOT-PLATE LATENCIES

| Treatment$^{a,b}$ | Tail-Flick Latency (sec) | Hot-Plate Latency (sec) |
|---|---|---|
| rhIGF-I Vehicle | 3.49 ± 0.15 | 8.72 ± 0.40 |
| Taxol Vehicle | 3.70 ± 0.30 | 7.34 ± 0.44 |
| rhIGF-I (1 mg/kg) | 3.43 ± 0.14 | 8.10 ± 0.39 |
| Taxol/rhIGF-I Vehicle | 4.99 ± 0.15* | 11.96 ± 0.54* |
| Taxol/rhIGF-I | 3.70 ± 0.19 | 7.74 ± 0.61 |

*Significantly different from vehicle, rhIGF-I or Taxol/rhIGF-I treated groups $p < 0.05$.
$^a$rhIGF-I Vehicle: The vehicle used for rhIGF-I was administered to one group of animals to serve as a control group, without rhIGF-I itself.
Taxol Vehicle: The vehicle used for Taxol was administered to one group of animals to serve as a control group, without Taxol itself.
rhIGF-I (1 mg/kg): rhIGF-I in its vehicle was administred as described.
Taxol/rhIGF-I Vehicle: Taxol in its vehicle was administered to one group of animals concurrently with the vehicle for rhIGF-I, but without rhIGF-I itself.
Taxol/rhIGF-I: Both taxol in its vehicle and rhIGF-I in its vehicle were administered as described.
$^b$Vehicle control groups are routinely performed to ensure that the vehicle carrying the agent to be tested has no effects on its own.

What is claimed is:

1. A method for the therapeutic reduction of a peripheral neuropathy that results from a toxic agent, wherein said toxic agent is a member of the group consisting of vincristine, cisplatin, and taxol wherein said peripheral neuropathy is not caused by an abnormal insulin level in a mammal, said method comprising administering 0.03–10 mg/kg/unit of insulin-like growth factor-I (IGF-I) to said mammal.

2. The method of claim 1, wherein said mammal is a human.

3. The method of claim 1, wherein said insulin-like growth factor-I is administered intravenously or subcutaneously.

4. The method of claim 1, wherein said insulin-like growth factor-I is administered simultaneously with said toxic agent.

5. The method of claim 4, wherein said toxic agent is vincristine.

6. The method of claim 4, wherein said toxic agent is taxol.

7. The method of claim 4, wherein said toxic agent is cisplatin.

8. The method of claim 5, wherein the weight to weight ratio of said insulin-like growth factor-I to said vincristine is between 1:400 and 75:1.

9. The method of claim 8, wherein said ratio is between 1:40 and 8:1.

10. The method of claim 1, wherein said insulin-like growth factor-I is administered to said mammal following toxic agent to restore at least a portion of the neurofunction destroyed by said toxic agent administration.

11. A composition comprising a substantially pure insulin-like growth factor-I and a toxic agent, wherein said toxic agent is a member of the group consisting of vincristine, cisplatin and taxol in a weight to weight ratio of between 1:400 and 75:1.

12. The method of claim 1, wherein said reducing comprises treating said peripheral neuropathy.

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 16
        ( B ) TYPE: amino acid
        ( C ) STRANDEDNESS:
        ( D ) TOPOLOGY: linear ( x i ) SEQUENCE DESCRIPTION: SEQ ID NO: 1:

Arg Arg Leu Glu Met Tyr Cys Ala Pro Leu Lys Pro Ala Lys Ser
    Ala

13. The method of claim 1, wherein said reducing comprises preventing said peripheral neuropathy.

* * * * *

UNITED STATES PATENT AND TRADEMARK OFFICE
CERTIFICATE OF CORRECTION

PATENT NO. : 5,420,112

DATED : May 30, 1995

INVENTOR(S) : Michael E. Lewis, et al

It is certified that error appears in the above-indentified patent and that said Letters Patent is hereby corrected as shown below:

On the title page insert item [73], Assignee should read as follows: --Cephalon, Inc., West Chester, Pennsylvania and Albert Einstein College of Medicine of Yeshiva University, Bronx, New York--; (a copy of the transmittal of issue fee and formal drawings filed December 9, 1994 is attached indicating the proper names of the above Assignee);

On the title page item [56], Attorney, Agent, or Firm should read as follows: --Fish & Richardson and Richard P. Burgoon, Jr.--; (this also was mentioned in the December 9, 1994 transmittal of issue fee and formal drawings);

UNITED STATES PATENT AND TRADEMARK OFFICE
CERTIFICATE OF CORRECTION

PATENT NO. : 5,420,112                     Page 2 of 2
DATED      : May 30, 1995
INVENTOR(S): Michael E. Lewis, et al It is certified that error appears in the above-indentified patent and that said Letters Patent is hereby corrected as shown below:

Col. 1, line 43, "andenvironmental" should read --and environmental--;

Col. 3, line 27, replace "penicillan" with --penicillin--;

Col. 7, line 67, after "denotes", add the following: "that the value is significantly different from both vehicles";

Col. 12, claim 1, line 16, after "unit", add --dose--.

Signed and Sealed this

Twenty-ninth Day of August, 1995

Attest:

BRUCE LEHMAN

Attesting Officer    Commissioner of Patents and Trademarks